US00PP36373P2

(12) United States Plant Patent
Neu

(10) Patent No.: US PP36,373 P2
(45) Date of Patent: Jan. 7, 2025

(54) ***PELARGONIUM* PLANT NAMED 'KLEIP23785'**

(50) Latin Name: *Pelargonium interpeltatum*
Varietal Denomination: KLEIP23785

(71) Applicant: KLEMM + SOHN GMBH & CO. KG, Stuttgart (DE)

(72) Inventor: Nina Neu, Weissach im Tal (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/585,907

(22) Filed: Feb. 23, 2024

(51) Int. Cl.
*A01H 5/02* (2018.01)
*A01H 6/42* (2018.01)

(52) U.S. Cl.
USPC ..... Plt./329
CPC ..... *A01H 6/425* (2018.05)

(58) Field of Classification Search
USPC ..... Plt./329
CPC ..... A01H 6/425; A01H 5/02
See application file for complete search history.

*Primary Examiner* — Keith O. Robinson
(74) *Attorney, Agent, or Firm* — Weatherly IP Solutions, LLC; James M. Weatherly

(57) ABSTRACT

A new *Pelargonium* plant particularly distinguished by purple flowers with a light flower center with dark purple red veins; no leaf zonation; and medium vigor, is disclosed.

1 Drawing Sheet

Genus and species: *Pelargonium interpeltatum.*
Variety denomination: 'KLEIP23785'.

BACKGROUND OF THE NEW PLANT

The present invention comprises a new and distinct variety of *Pelargonium*, botanically known as *Pelargonium interpeltatum* and hereinafter referred to by the variety name 'KLEIP23785'. 'KLEIP23785' originated from a controlled cross in August 2018 in Nairobi, Kenya between the proprietary female *Pelargonium* variety 'PIP-2015-5426' (unpatented) and the proprietary male *Pelargonium* variety 'PZ-2016-6208' (unpatented).

Seeds from the controlled-cross were obtained. The seeds were sown and plants were grown for evaluation. A single plant was selected in June 2019 and subsequently named 'KLEIP23785'. In July 2019 'KLEIP23785' was first vegetatively propagated by vegetative stem cuttings in Stuttgart, Germany. 'KLEIP23785' was found to reproduce true to type in successive generations of asexual propagation via stem cuttings in Stuttgart, Germany.

SUMMARY

The following are the most outstanding and distinguishing characteristics of this new variety when grown under normal horticultural practices in Stuttgart, Germany.

1. Purple flowers with a light flower center with dark, purple-red veins;
2. No leaf zonation; and
3. Medium vigor.

DESCRIPTION OF THE PHOTOGRAPH

This new *Pelargonium* plant is illustrated by the accompanying photograph which shows an overall view of the plant in a pot. The photograph is of an approximately 20-week-old plant grown outdoors in Stuttgart, Germany, in August 2022. The colors shown are as true as can be reasonably obtained by conventional photographic procedures.

DESCRIPTION OF THE NEW VARIETY

The following detailed descriptions set forth the distinctive characteristics of 'KLEIP23785'. Data was collected on 15-week-old plants in Stuttgart, Germany, under greenhouse conditions in February 2024. Color references are to The R.H.S. Colour Chart of The Royal Horticultural Society of London (R.H.S.), 5$^{th}$ edition (2007).

Classification:
- *Family.*—Geraniaceae.
- *Botanical.*—*Pelargonium interpeltatum.*
- *Common.*—*Pelargonium.*
- *Designation.*—'KLEIP23785'.

Parentage:
- *Female parent.*—PIP-2015-5426 (interspecific, unpatented).
- *Male parent.*—PZ-2016-6208 (*P.* x *hortorum*, unpatented).

Plant:
- *Form.*—Bushy.
- *Habit.*—Mounding.
- *Height (from top of soil).*—18.0 cm.
- *Width (horizontal plant diameter).*—28.0 cm.
- *Natural flowering season.*—March to October.
- *Propagation type.*—Vegetative by stem cuttings.
- *Time to produce a finished flowering plant.*—12 weeks.
- *Time to initiate and develop roots.*—4 weeks.
- *Root description.*—Fine, dense, white RHS 158A.
- *Flower type.*—Zygomorphic.

Stems:
- *Quantity of stems per plant.*—7-10.
- *Color.*—RHS144B.
- *Surface texture.*—Pubescent.
- *Stem form.*—Round.
- *Diameter.*—0.6 cm.

*Length.*—6.0 to 8.0 cm.
*Internode length.*—0.5 cm.
*Anthocyanin.*—Absent.

Leaves:
*Arrangement.*—Alternate.
*Shape.*—Reniform.
*Apex.*—Round.
*Base.*—Open.
*Margin.*—Crenate.
*Surface texture both surfaces.*—Pubescent.
*Length.*—4.5 cm.
*Width.*—6.5 cm.
*Color.*—Upper surface: RHS 139A. Lower surface: RHS 137C.
*Zonation.*—None.
*Depth of sinus.*—1.5 cm.
*Petiole.*—Length: 2.7 cm. Diameter: 0.2 cm. Color: RHS 143A. Strength: Medium.
*Venation pattern.*—Palmate.
*Venation color.*—Upper surface: RHS 137A. Lower surface: RHS 143A.

Inflorescence:
*Lastingness of flowers on the plant.*—6 to 8 days.
*Umbels.*—Quantity of umbels per plant: 14. Length: 4.5 cm. Diameter: 8.0 cm.
*Individual florets of the umbel.*—Quantity of florets per umbel: 13 to 20. Depth: 2.5 cm. Diameter: 4.4 cm.
*Fragrance.*—Absent.

Flower buds:
*Cluster shape.*—Round.
*Cluster size.*—Length: 1.5 cm. Width: 2.0 cm.
*Surface texture.*—Pubescent.
*Bud.*—Height: 1.0 cm. Width: 0.5 cm. Shape: Round. Apex: Acute. Base: Obtuse. Margin: Entire. Color: RHS 143A.

Petals:
*Quantity per flower.*—5.
*Shape.*—Spatulate.
*Apex.*—Round.
*Base.*—Obtuse.
*Margin.*—Entire.
*Length.*—2.4 cm.
*Width.*—1.9 cm.
*Surface texture.*—Upper surface: Smooth. Lower surface: Smooth.
*Color of lobes.*—Upper lobes: Upper surface: Closest to RHS N78 A. Lower surface: RHS N78B. Lower lobes: Upper surface: closest to RHS N78A. Lower surface: RHS N78B.
*Markings.*—Present; dark veins (RHS 71A) on upper and lower lobes, and lighter colored base of upper lobes (RHS 75A) with size of 1.1 cm from the base of the lobe.

Petaloids:
*Quantity per flower.*—0 to 3.
*Shape.*—Crippled and very small, closest to lanceolate.
*Apex.*—Acute.
*Base.*—Obtuse.
*Margin.*—Entire.
*Length.*—0.3 cm.
*Width.*—0.1 cm.
*Surface texture.*—Upper surface: Smooth. Lower surface: Smooth.
*Color.*—Upper surface: Closest to RHS N78A. Lower surface: RHS N78B.

Sepals:
*Number per flower.*—5.
*Shape.*—Elliptic.
*Apex.*—Acute.
*Base.*—Obtuse.
*Margin.*—Entire.
*Surface texture.*—Upper surface: Smooth. Lower surface: Pubescent.
*Color.*—Upper surface: RHS 59B at base and RHS 143A at tip. Lower surface: RHS 59B at base and RHS 143A at tip.
*Length.*—1.1 cm.
*Width.*—0.4 cm.

Pedicel:
*Length.*—1.8 cm.
*Diameter.*—0.1 cm.
*Color.*—RHS 59A.
*Surface texture.*—Pubescent.
*Strength.*—Soft.

Peduncle:
*Length.*—11.5 cm.
*Diameter.*—0.3 cm.
*Color.*—RHS 143B.
*Texture.*—Pubescent.
*Strength.*—Medium.

Reproductive organs:
*Stamens.*—Quantity per flower: 3-7. Anther length: 0.2 cm. Filament length: 0.6 cm. Filament color: RHS N74B at tip and RHS NN155D at base. Pollen amount: Abundant. Pollen color: RHS N25A.
*Pistils.*—Number: 1.Stigma color: RHS 59B. Style length: 0.3 cm. Style color: RHS 59B. Ovary arrangement: Central. Ovary color: RHS 143B. Ovary diameter: 0.3 cm. Ovary length: 0.5 cm. Ovary Texture: Pubescent.

Fruit and seed set: None.
Disease and pest/insect resistance: None.

COMPARISON WITH PARENTAL LINES AND KNOWN VARIETY

'KLEIP23785' is distinguished from its parents as described in Table 1.

TABLE 1

Comparison with Parental Lines

| Characteristic | 'KLEIP23785' | Female parent | Male parent |
|---|---|---|---|
| Flower marking | Light flower center and veins | Red spots and veins | No marking |
| Leaf zonation | None | Weak | None |
| Vigor | Medium | Very low vigor | Vigorous |

'KLEIP23785' can be compared to the commercial variety 'Calliope L Lavender Rose' (patent status unknown). Differences between the two varieties are described in Table 2:

TABLE 2

| Comparison with Similar Variety | | |
|---|---|---|
| Trait | Variety 'KLEIP23785' | Commercial line 'Calliope L Lavender Rose' |
| Marking | Lighter center and dark purple red veins | Red veins and spot with white center |

TABLE 2-continued

| Comparison with Similar Variety | | |
|---|---|---|
| Trait | Variety 'KLEIP23785' | Commercial line 'Calliope L Lavender Rose' |
| Leaf color | Dark green | Green |
| Vigor | Medium | Vigorous |

I claim:

1. A new and distinct cultivar of *Pelargonium* Plant Named 'KLEIP23785' as described and illustrated herein.

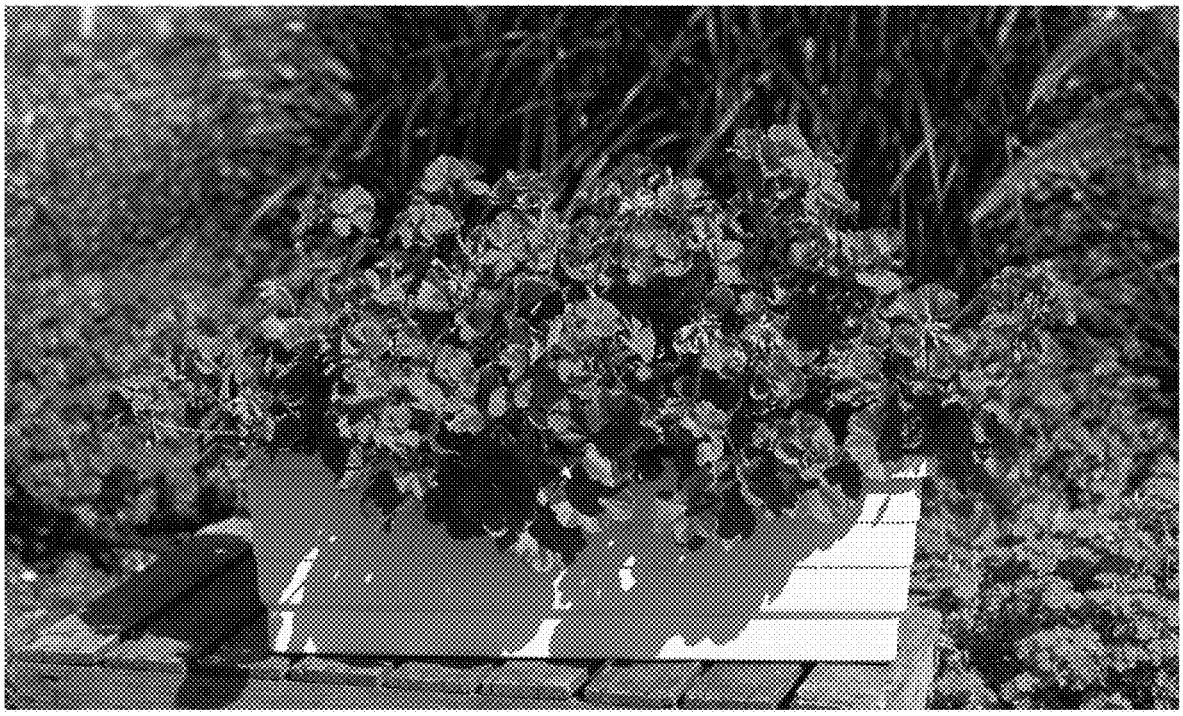

* * * * *